United States Patent [19]

Adair

[11] Patent Number: 4,914,521
[45] Date of Patent: Apr. 3, 1990

[54] STERILIZABLE VIDEO CAMERA COVER

[76] Inventor: Edwin L. Adair, 2800 S. University Blvd., Denver, Colo. 80210

[21] Appl. No.: 306,809

[22] Filed: Feb. 3, 1989

[51] Int. Cl.$^4$ ............................................. H04N 5/30
[52] U.S. Cl. ...................................... 358/229; 358/98; 128/6
[58] Field of Search ...................... 358/98, 229; 128/4, 128/6, 846, 849; 354/62

[56] References Cited

U.S. PATENT DOCUMENTS

| | | |
|---|---|---|
| 2,132,549 | 10/1938 | Wenstrom . |
| 2,537,303 | 1/1951 | Cobb, Jr. et al. . |
| 3,026,784 | 3/1962 | Byers . |
| 3,821,759 | 6/1974 | Vooght . |
| 4,590,923 | 5/1986 | Watanabe ............................... 358/98 |
| 4,646,722 | 3/1987 | Silversteh et al. ...................... 128/4 |
| 4,722,000 | 1/1988 | Chateneve ............................ 358/98 |
| 4,756,304 | 7/1988 | Watanabe ............................... 128/6 |
| 4,757,381 | 7/1988 | Cooper et al. ......................... 358/98 |

Primary Examiner—Jin F. Ng
Assistant Examiner—Magdy Shehata
Attorney, Agent, or Firm—Fields, Lewis, Pittenger & Rost

[57] ABSTRACT

A sterilizable video camera cover is provided which has a connector having a guideway for receiving an unsterile video camera within it is a predetermined fixed orientation. A receptacle is provided for holding the camera in this position against a window at the distal end of the connector which serves as a bacteria barrier. A flared end is provided distally of the window for receiving a sterile "C" mount and endoscope in a fixed position with respect to the camera. An accordion folded sleeve is positioned on the receptacle for being extended over the trailing cable of the video camera to maintain the sterile environment within the operating room even though the camera and trailing cable are unsterile.

9 Claims, 2 Drawing Sheets

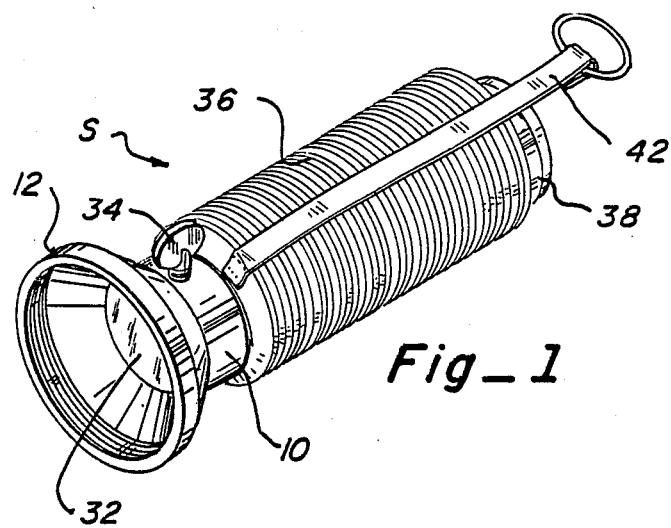
Fig_1
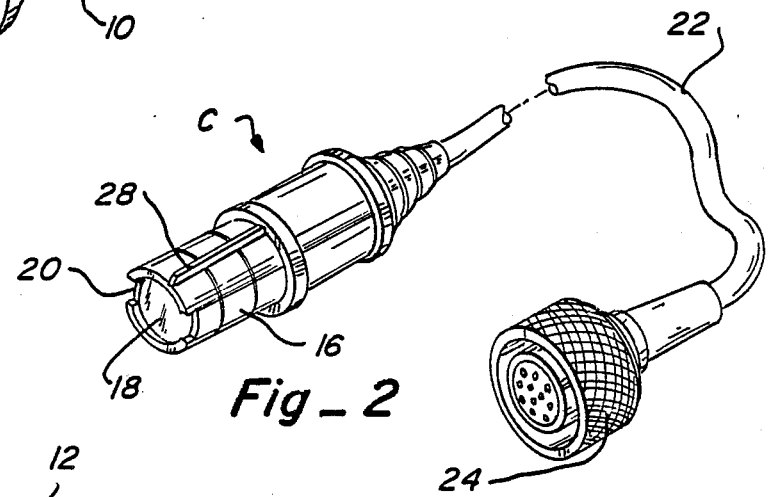
Fig_2
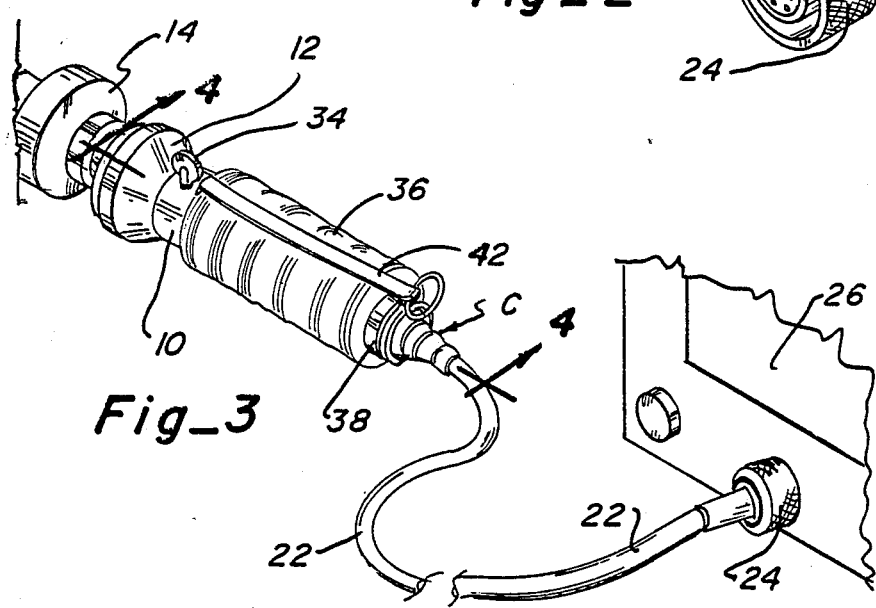
Fig_3

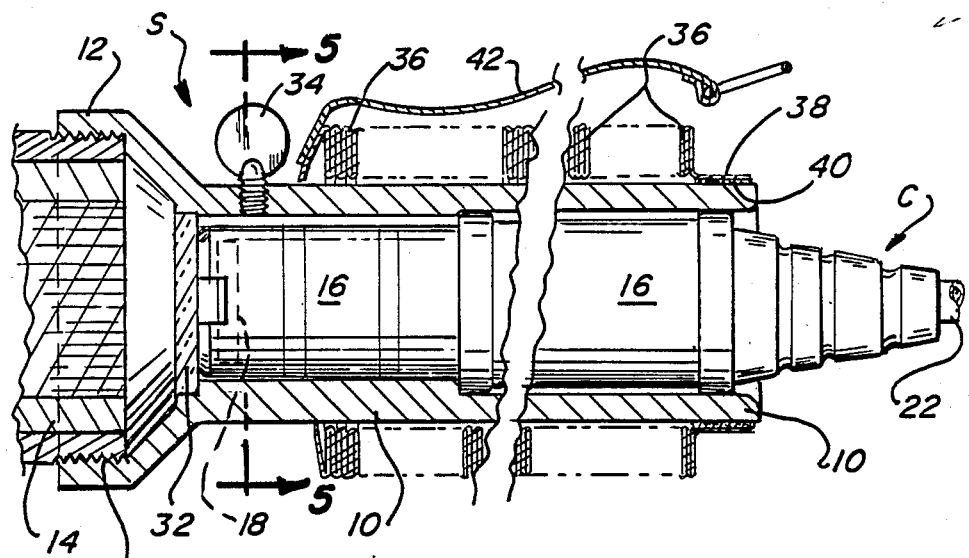
Fig_4
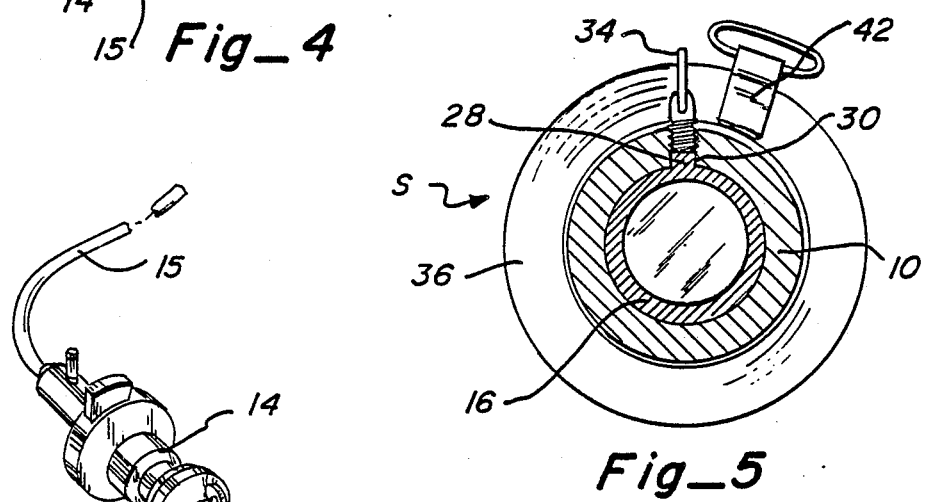
Fig_5
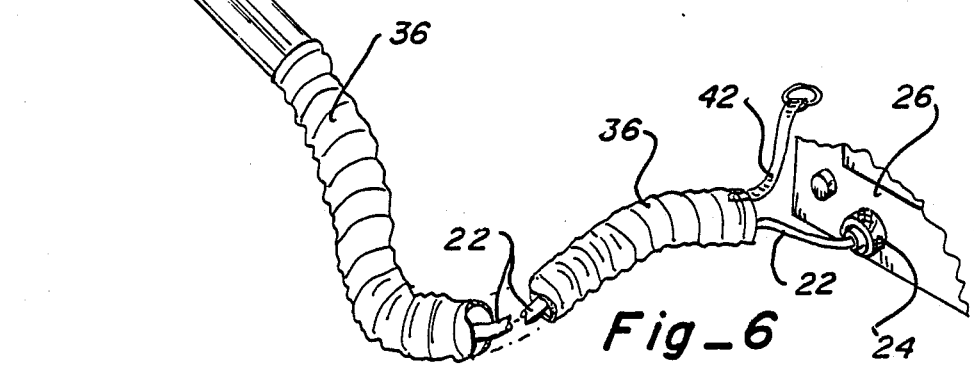
Fig_6

STERILIZABLE VIDEO CAMERA COVER

TECHNICAL FIELD

This invention relates to a sterilizable video camera cover for use in an operating room environment and more particularly to such a cover which encloses and aligns an unsterile camera with a sterile "C" mount or beam splitter or other connecting type optical device and hence to a sterile endoscope.

BACKGROUND ART

For many years, unsterile cameras have been used in surgery by placing them into a sterile plastic bag or drape which has an opening in one end which fits around the camera attachment to mate to an optical connector called a "C" mount. However, the act of aligning the unsterile camera within the drape or bag for connecting to a "C" mount which fits through the hole in the drape and is threaded into the camera housing can create contamination. This always occurs if the connecting optic, such as a "C" mount must be replaced with a beam splitter or other device such as a different focal length "C" mount. Such manipulations do not preserve sterile integrity.

A sterile pouch for containing a standard still picture camera for use in an operating room is shown in U.S. Pat. No. 2,537,303 to Cobb, Jr. et al. However, there is no thought in this device of connecting the camera to other optical means.

Other containers for protecting cameras for underwater photography are shown in U.S. Pat. No. 3,026,784 to Byers and in U.S. Pat. No. 3,821,759 to Vooght. Another camera case for protecting a camera during use is shown in U.S. Pat. No. 2,132,549 to Wenstrom. However, none of these are intended for use in an operating room to maintain the environment within the operating room in a sterile condition even when the camera is not sterile.

If properly constructed, the camera itself can be made sterile by soaking it in a sterilizing solution or through low temperature gas sterilization. However, a camera which can withstand such procedures, without being damaged, is very expensive so that many hospitals and small clinics can not afford it. However, small cameras are available which would be satisfactory for use in the surgical area if they can be placed in a sterile drape or cover which will maintain the surgical area in a sterile condition and which cover can be removed and disposed of after each operation and replaced with another similar sterile cover for the next operation.

DISCLOSURE OF THE INVENTION

An apparatus is provided for enclosing a non-sterile video camera and trailing cable in a sterile enclosure for use of the camera in the sterile environment of an operating room. The apparatus includes a generally cylindrical housing having an outer surface and an inner surface with a diameter of a size to snugly receive a camera through a first open end. A transparent window is mounted at a second end of the housing which is contacted by the end of the camera when the camera is in place. Means is provided for aligning the camera within the housing in a fixed position. A flared annular mounting is attached and extends from the second end of the housing. Means are provided for attaching an optical transmitting means to the mounting to provide light images to the camera through the window. A sleeve is attached to the outer surface of the housing which is extended back over the trailing cable of the camera for a substantial distance. The aligning means comprises a longitudinal slot in the inner surface of the sterile housing for receiving a corresponding rib on the camera. A set screw is provided for locking the camera in position against the window. The attaching means can comprise internal threads for receiving a "C" mount or beam splitter, the threads being clocked to properly align the optical transmitting means when it is fully tightened. The sterile sleeve is arranged in an accordion shape over the housing prior to use.

Stated another way, the invention includes a sterile enclosure for a video camera and trailing cable when in use in an operating room. This enclosure includes a generally cylindrical connector for interconnecting a sterile "C" mount and endoscope to a non-sterile video camera, the connector including a first end for attachment to the proximate end of the "C" mount and endoscope and a second end with a receptacle for receiving the camera and a transverse window between the endoscope and "C" mount connector and the receptacle. Means is provided to fix the orientation between the "C" mount and endoscope and the camera and flexible sterile means on the connector extend over the camera and a substantial portion of the trailing cable. The first end of the connector is flared and has a greater diameter than the second end. A longitudinal groove is provided in the receptacle for receiving a rib on the camera to properly orient the camera within the connector. Clocked internal threads on the first end for connecting the "C" mount and endoscope in a predetermined orientation with the camera are provided. The flexible means includes an accordion folded sleeve received over the receptacle, means attaching the end of the sleeve adjacent the proximate end of the receptacle and a pull tab on the distal of the sleeve for pulling the sleeve down over itself and along the trailing camera cable.

With the cover just described, it is possible to use an inexpensive camera in a sterile operating room environment and still maintain the requisite sterility. The sterile "C" mount and endoscope are separated from the unsterile camera by the window which serves as a barrier to bacteria and all contamination. The camera and trailing cable are covered by the sleeve to provide a bacteria barrier to the operating area.

Additional advantages of this invention will become apparent from the description which follows, taken in conjunction with the accompanying drawings.

BRIEF DESCRIPTION OF THE DRAWINGS

FIG. 1 is a perspective view of a sterilizable video camera cover constructed in accordance with this invention;

FIG. 2 is a perspective view of a video camera for use within the video camera cover of FIG. 1;

FIG. 3 is a perspective view showing the camera of FIG. 2 installed in the camera cover of FIG. 1;

FIG. 4 is an enlarged, fragmentary longitudinal section, taken along line 4—4 of FIG. 3, showing how the camera interconnects with the camera housing;

FIG. 5 is a vertical section, taken along line 5—5 of FIG. 4, showing further details of the invention; and FIG. 6 is a perspective view similar to FIG. 3 but showing the cover extended along the trailing cable of the video camera.

BEST MODE FOR CARRYING OUT THE INVENTION

Typically a sterile endoscope is connected by means of a "C" mount to a sterile camera. The distal end of the endoscope can be introduced into an internal body site for viewing. The maintenance of sterility is critical.

In accordance with this invention a disposable sterilizable cover S, as shown in FIG. 1, is provided for use with the unsterile camera C shown in FIG. 2 to provide a bacteria barrier between the unsterile camera and a sterile endoscope. The overall structure of cover S can best be seen by viewing FIGS. 1 and 4. It comprises a sterile cylindrical housing or sheath 10 for receiving camera C, as described below and includes a flared annular mounting 12 into which an optical transmitting means, such as a "C" mount 14 and endoscope 15, can be threadably received. The distal end of the endoscope placed at a site under investigation within the body of a patient.

The camera C has a body 16 having a distal end with a lens 18 and a coupling 20 which spaces camera C from window 32 inside of sterile sheath 10. The proximate end of body 16 includes a cable 22 having appropriate wiring for transmitting a signal from the camera to a connector 24 for attachment to a video processing unit 26 so that an image picked up by camera C can be processed and viewed on a monitor (not shown).

Conveniently, the camera body 16 is provided with a longitudinal rib 28 which is aligned with and received within a longitudinal groove 30 of cylindrical housing 10, as best seen in FIGS. 4 and 5. The camera is inserted in housing 10 as far forwardly as possible so that the lens 18 is as close as possible to transverse window 32 which separates camera 16 from "C" mount 14 and endoscope 15 and serves as a bacteria barrier between the sterile catheter and the unsterile camera. The camera is held firmly in position by means of set screw 34 which is aligned with rib 28, both of these being at the twelve o'clock position. Thus, the camera will always be oriented in the same manner with respect to housing 10 and held in place by the thumb screw. Also, the twelve o'clock position of the thumb screw will provide a reference for the doctor to know when he has the camera in an upright position, and particularly when he is working in a dark operating room.

A sleeve 36 having accordion folds is placed over housing 10, as shown, and has a flange 38 with an adhesive backing or tape 40 for attachment to the proximate end of cylindrical housing 10. Prior to use, this sleeve extends longitudinally from the proximate end toward the distal end as shown and has a pull strap 42 for pulling the sleeve inside out over the end of the camera and cable 22 for a considerable distance, such as 8', or 10', Conveniently, annular mounting 12 is provided with internal threads 15 which are clocked so that when "C" mount and endoscope 14 are attached thereto, the catheter will have a specific orientation with respect to housing 10 and camera C when all parts are assembled together so that the image viewed by the endoscope will always be in the proper orientation with respect to the camera and provide an image properly oriented on the video monitor.

The housing 10 and annular mounting 12 can be made out a suitable plastic or metal material and the sleeve 36 can be made out of a plastic, all of which is sterilized by gas sterilization or radiation sterilization before use. Suitable plastics are polyvinyl chloride and high impact polystyrene. Stainless steel or aluminum are suitable metals. The "C" mount and endoscope, which are also sterile can then be attached to the mounting 12. The camera, which is not sterile, is inserted within housing 10, as previously described and held in position by set screw 34, then pull tab 42 is pulled so that sleeve 36 is pulled back over itself and extended along cable 22 which is not sterile for a significant distance, such as 8' or 10'. Thus, the unsterile camera is covered by sterile sleeve 36 as is the trailing cable for a sufficient distance that the camera can be used in the operating room without compromising the sterility in the operating area. After use, the camera and endoscope are disconnected and the sterilizable cover is thrown away and a new sterile one is used for the next operation. With this apparatus, a camera can be used which does not need to be sterilized through heating, soaking or other sterilizing proceedings. Since it does not need to be waterproof, it can be a much less expensive camera making the combined device, which includes a camera, "C" mount and endoscope available at much lower cost to medical clinics and hospitals who otherwise would not be able to afford the apparatus.

This invention has been described in detail with reference to a particular embodiment thereof, but it will be understood that various other modifications can be effected within the spirit and scope of this invention.

What is claimed:

1. An apparatus for enclosing a non-sterile video camera and its trailing cable in a sterile enclosure for use of the camera in the sterile environment of an operating room, said apparatus comprising:

a generally cylindrical housing having an outer surface and an inner surface with a diameter of a size to snugly receive a camera through a first open end;

a transparent window mounted at a second end of said housing which is contacted by the end of the camera;

means for aligning the camera within said housing in a fixed position;

a flared annular mounting attached to and extended from said second end of said housing;

means for attaching an optical transmitting means to said mounting to provide light images to the camera through said window; and a sleeve attached to said outer surface of said housing extendable over the trailing cable of the camera for a substantial distance.

2. Apparatus, as claimed in claim 1, wherein:

said aligning means comprises a longitudinal slot in the inner surface for receiving a corresponding rib on the camera.

3. Apparatus, as claimed in claim 1, further including:

a set screw for locking the camera in position against said window.

4. Apparatus, as claimed in claim 1, wherein:

said attaching means comprises internal threads for receiving a "C" mount, said threads being clocked to properly align the optical transmitting means when it is fully tightened.

5. Apparatus, as claimed in claim 1, wherein:

said sleeve is arranged in accordion shape over said housing prior to use.

6. A sterile enclosure for a video camera and trailing cable when in use in an operating room, said enclosure comprising:

a generally cylindrical connector for interconnecting a sterile "C" mount and endoscope, having a proximate end, to a non-sterile video camera, said connector including a first end for attachment to the proximate end of the "C" mount, a second end with a receptacle for receiving the camera and a transverse window between said connector and said receptacle;

means for providing a fixed orientation between the "C" mount and the camera; and flexible sterile means on said connector extendable over the camera and a substantial portion of the trailing cable.

7. Apparatus, as claimed in claim 6, wherein:

said first end of said connector is flared and has a greater diameter than said second end.

8. Apparatus, as claimed in claim 7, wherein said providing means includes:

a longitudinal groove in said receptacle for receiving a rib on the camera;

clocked internal threads on said first end for connecting the "C" mount in a predetermined orientation with the camera.

9. Apparatus, as claimed in claim 6, wherein said flexible means includes:

an accordion folded sleeve received over said receptacle;

means attaching the end of said sleeve adjacent the proximate end of said receptacle; and a pull tab on the distal end of said sleeve for pulling the sleeve down over itself and along the trailing camera cable.

* * * * *